United States Patent [19]

Alexander

[11] Patent Number: 4,512,183

[45] Date of Patent: Apr. 23, 1985

[54] METHOD OF MEASURING AND/OR MONITORING THE SURFACE TENSION OF FLUIDS

[76] Inventor: Martin Alexander, Wilhelm-Kuhnert-Str. 24, 8000 München 90, Fed. Rep. of Germany

[21] Appl. No.: 522,180

[22] PCT Filed: Jan. 18, 1983

[86] PCT No.: PCT/EP83/00013

§ 371 Date: Aug. 1, 1983

§ 102(e) Date: Aug. 1, 1983

[87] PCT Pub. No.: WO83/02500

PCT Pub. Date: Jul. 21, 1983

[51] Int. Cl.³ .............................................. G01N 13/02
[52] U.S. Cl. ...................................... 73/64.4; 356/445
[58] Field of Search ................. 73/64.4; 356/445, 446, 356/447, 448

[56] References Cited

U.S. PATENT DOCUMENTS 3,068,687 12/1962 Kleine et al. ......................... 73/64.4

FOREIGN PATENT DOCUMENTS 823980 4/1981 U.S.S.R. .............................. 73/64.4

*Primary Examiner*—Howard A. Birmiel
*Assistant Examiner*—Joseph W. Roskos
*Attorney, Agent, or Firm*—Learman & McCulloch

[57] ABSTRACT

The invention relates to a method for measuring and/or monitoring the surface tension of fluids in which a circular region of the surface of the fluid is excited to oscillation, a system of circular standing capillary waves is produced and this is determined by measuring the intensity of reflected light radiation. Such a method is distinguished by simple operation and is also suitable for automatic monitoring of surface tension.

8 Claims, 7 Drawing Figures

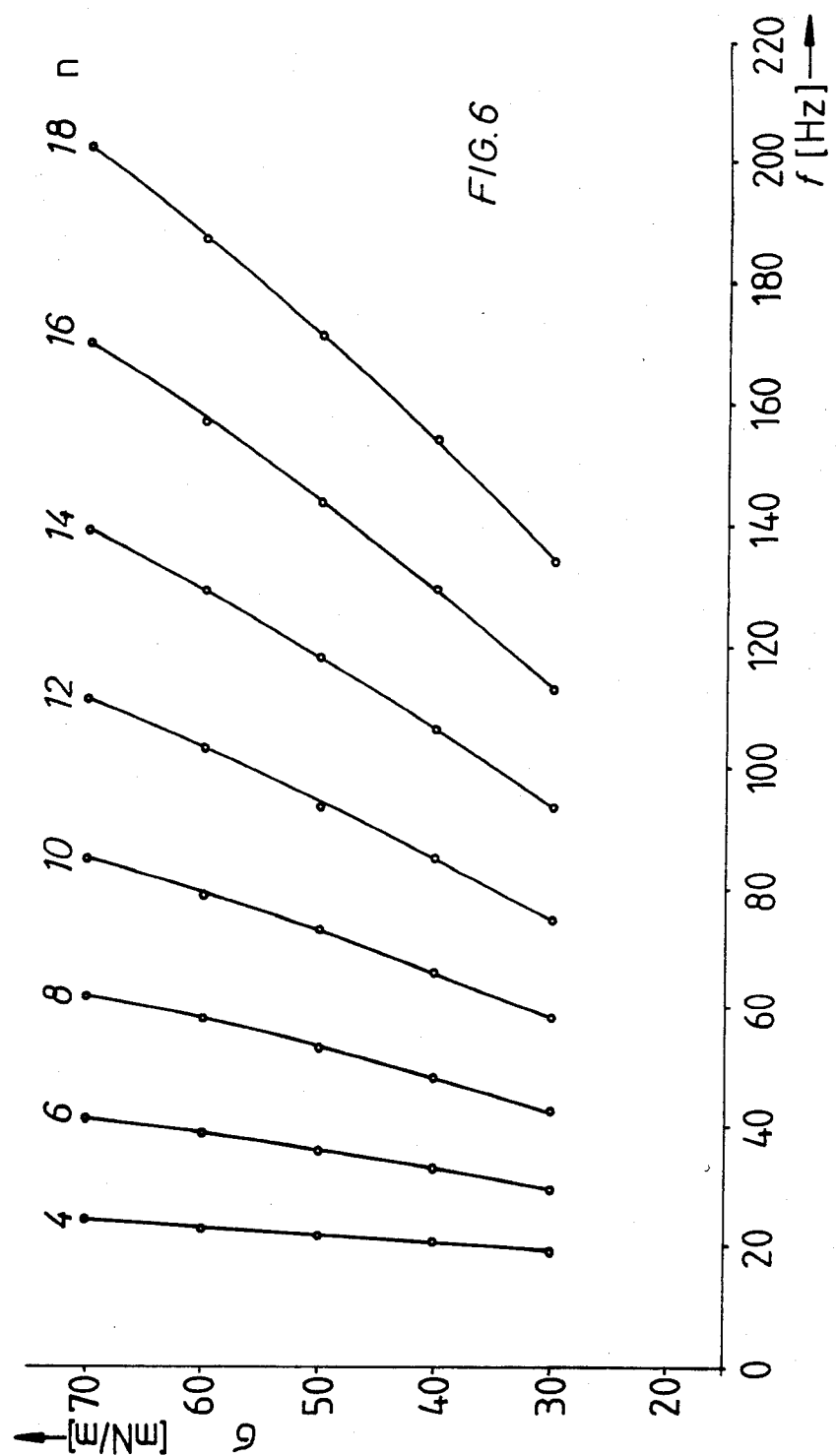

METHOD OF MEASURING AND/OR MONITORING THE SURFACE TENSION OF FLUIDS

The invention relates to a method of measuring and-/or monitoring the surface tension of fluids, in which standing capillary waves are produced on the surface of the fluid by means of an oscillation generator of a known frequency and are optically evaluated.

The surface tension of many organic substances is reduced when they are dissolved in water. This applies for example to alcohols, organic acids and salts thereof. Even small quantities of such substances make themselves clearly noticeable in their effect on the surface tension. Therefore by measuring the surface tension it is possible to determine the presence and the quantity of certain substances in the fluid.

For measuring the surface tension of fluids the capillary wave method is known amongst others (cf. in this connection MULLER-POUILLET, Lehrbuch der Physik, Vol. III/1, pages 548 to 551). In this known method a tuning fork of known period of oscillation has two fine points which dip into the fluid and is used to produce waves on the surface of the fluid which interfere with each other and therefore produce distinct standing waves in their connecting lines. Their length can be determined by means of a microscope with a long focal distance.

With a known frequency and wavelength, the surface tension can be calculated using the formula developed from the theory of capillary waves:

$$\sigma = \frac{1}{2\pi} \cdot \rho \cdot \nu^2 \cdot \lambda^3 - \frac{g \cdot \lambda^2 \cdot \rho}{4\pi^2}$$

$\sigma$ = surface tension
$\chi$ = density
$\nu$ = oscillation frequency
$g$ = acceleration due to gravity
$\lambda$ = wavelength A significant disadvantage of this known method lies in the very complicated optical evaluation of the standing capillary waves by means of a microscope.

The object of the invention, therefore, is to avoid this disadvantage and provide a method of the type described in the introduction which is distinguished by its particularly simple operation and is also suitable for automatic monitoring of the surface tension of fluids.

This object is achieved according to the invention by the following features:

(a) a circular region of the surface of the fluid is excited centrally or peripherally by the oscillation generator;
(b) the wavelength of the capillary waves thus produced or the radius of the excited circular surface region is altered until a system of circular standing capillary waves is produced;
(c) the occurrence of circular standing capillary waves is determined by measuring the intensity of light radiation reflected on the surface of the fluid.

The central or peripheral excitation of the circular region of the surface of the fluid used for the measurement (conveniently in a measuring vessel with a circular wall) results at a certain wavelength of the capillary waves in a system of circular standing waves. These occur when the radius of the circular measuring vessel is an integral multiple of half the wavelength.

The occurrence of these circular standing capillary waves can be determined in a simple manner according to the invention by monitoring the intensity of light radiation reflected on the surface of the fluid. At the frequency at which the circular standing capillary waves occur, a minimum defined as a sharp peak is produced in the intensity of the reflected light radiation.

This makes it possible either to monitor the surface tension of the fluid for any deviations from a predetermined original or theoretical value or—after prior calibration of the measuring device—to make a quantitative measurement of the surface tension.

It is a considerable advantage of the method according to the invention that the measurement and/or monitoring of the surface tension of the fluid does not require any complicated optical evaluation of the surface appearance by means of a microscope. The measuring method according to the invention is therefore also suitable for remote measurement or remote monitoring—an invaluable advantage for many applications.

One sphere of application of the method according to the invention is in the monitoring of the purity of water within the framework of environmental protection.

Another technical sphere of application is in the control of the alcohol content in the moistening means in offset printing.

In order to achieve standing capillary waves, the wavelength of the generated waves can be altered according to the invention by altering the frequency of the oscillation generator—whilst keeping the diameter of the excited circular surface region constant.

Another possibility for producing standing capillary waves is to alter the radius of the excited circular surface region—whilst keeping the frequency of the oscillation generator constant. This can be achieved for example by altering the filling level of a conical measuring vessel.

The invention will be described in greater detail with the aid of the drawings.

FIG. 6 is a chart showing a plurality of calibration curves.

Figure 1:
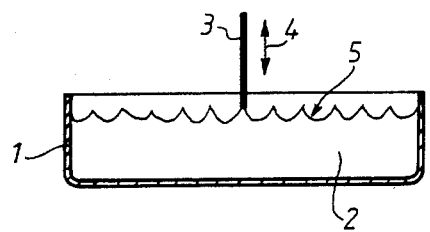
FIG. 1 is a sectional, diagrammatic view of one embodiment of apparatus for use in performing the method.
Figure 2:
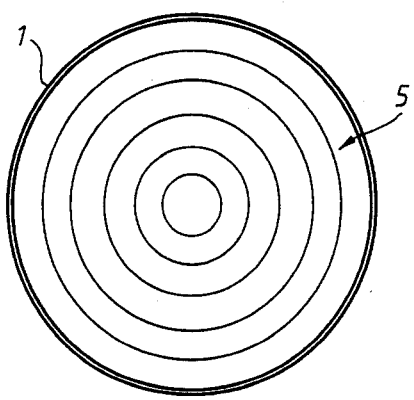
FIG. 2 is a top plan view.

FIG. 1 shows a measuring vessel 1 of circular cross-section which contains a fluid sample 2 into which an oscillation generator 3 dips centrally. If desired, the vessel may be conical as shown in FIG. 4A. This oscillation generator 3 is set in vertical oscillation (arrow 4) by an arrangement of variable frequency which is not shown. At a specific frequency of the oscillation generator 3 circular standing capillary waves are produced (cf. FIG. 2) on the surface 5 of the fluid sample 2.

Figure 3:
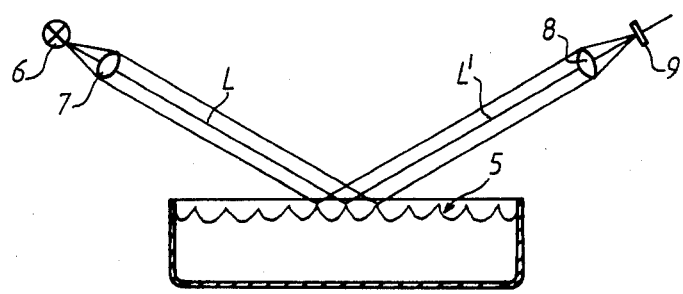
FIG. 3 is a view similar to FIG. 1, but illustrating additional apparatus.

A light source 6 casts a beam of light L via an optical system 7 onto the surface 5 of the fluid sample 2 (the light radiation covers the range of several wave trains). The light beam L' reflected on the surface passes via an optical system 8 to a sensor 9 which measures the intensity of the reflected light radiation (cf. FIG. 3).

If the frequency f of the oscillation generator 3 is then varied and the intensity U of the reflected light radiation received by the sensor 9 is determined, then at specific frequencies $f_1$, $f_2$, etc. (cf. FIG. 5) a minimum intensity defined as a sharp peak is determined. At these frequencies a system of circular standing capillary waves is present on the surface 5 of the fluid sample 2 (here the radius of the measuring vessel 1 amounts in each case to an integral multiple of half the wavelength, i.e. the distances between the common lines of the standing waves).

Figure 4:
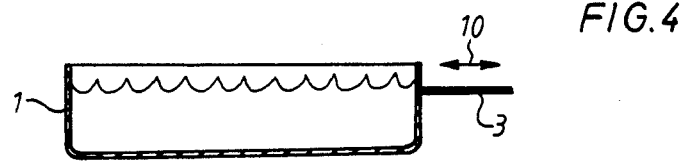
FIG. 4 is a view similar to FIG. 1, but illustrating a modification.
Figure 4A:
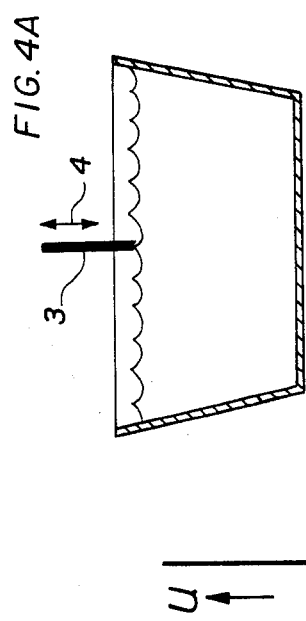
FIG. 4A is a view similar to FIG. 1, but illustrating a further modification.

FIG. 4 shows schematically the case in which the surface oscillation is not excited centrally but peripherally (on the periphery of the circular measuring vessel 1) by the oscillation generator 3 which is set in horizontal oscillation (arrow 10).

For monitoring the surface tension it is frequently sufficient merely to determine any deviation of the frequency (from a predetermined original or theoretical value) at which the system of circular standing capillary waves occurs.

Furthermore, for a quantitative measurement of the surface tension calibration of the measuring device is necessary. In order to determine the relationship between the frequency f at which the standing capillary waves occur and the respective surface tension $\sigma$, the frequency and the wavelength at which standing capillary waves occur is determined for several fluid samples of different surface tension and from this the surface tension is calculated according to the formula set out above.

In this way the calibration curves reproduced in FIG. 6 are arrived at. They apply to a measuring vessel with a circular cross-section and a radius of 2 cm for fluids having the density $\rho = 1$. The surface tension $\sigma$ is plotted (in mN/m) in the ordinate and the frequency f is plotted (in Hz) in the abscissa. n shows the number of circular standing capillary waves in the measuring vesel.

The wavelength on occurrence of standing capillary waves can be determined (for calibration purposes) either by counting the common lines or wave peaks which occur (within the known vessel diameter) or by microscopic evaluation of several wave trains.

Figure 5:
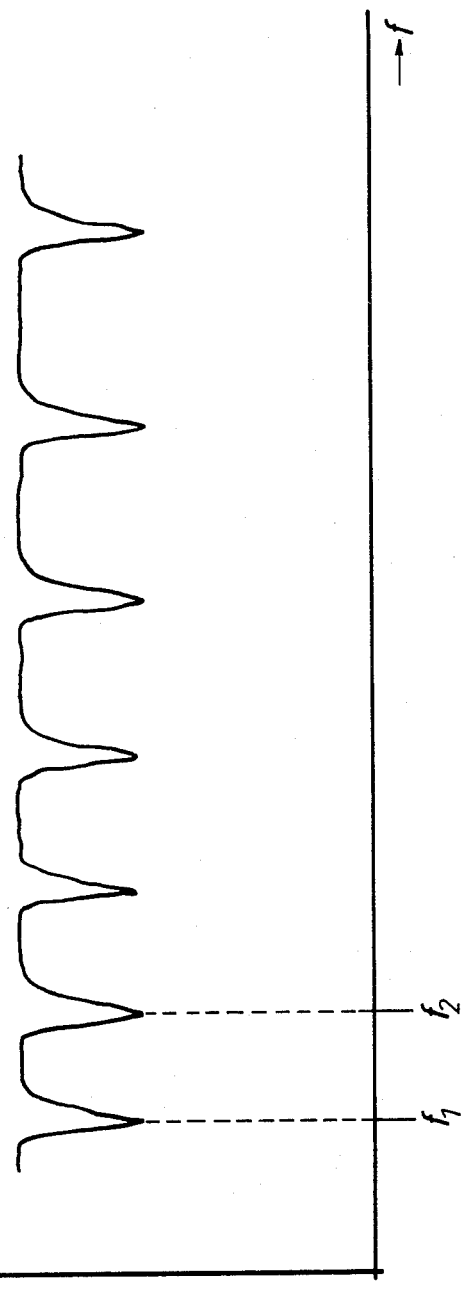
FIG. 5 is a graph.

The following practical examples serve for further explanation of the invention:

1. In the case of FIG. 5 a measuring vessel with a circular cross-section and a radius of 2 cm is used. The fluid under examination has a density $\rho = 1$ and a surface tension of 70 mN/m. The minima to be observed occur at the following frequencies: 24.5, 32.5, 41.5, 51, 62, 73, 85, 98, 111, 125, 139, 154, 170 Hz.

2. In a fluid having the density $\rho = 1$ and a surface tension of 70 mN/m $\lambda = 0.5$ cm. $\lambda/2$ thus amounts to 0.25 cm. In a conical vessel with a surface radius r=2 cm eight circular standing waves with a common line spacing of $\lambda/2$ are produced at this frequency. With any increase or reduction in the surface radius (by altering the filling level of the conical measuring vessel) by $\lambda/2$ or by a multiple of this value standing capillary waves can be observed again. In this way $\lambda$ is known. The constant frequency f of the oscillation generator is predetermined. In this way the surface tension can be calculated.

I claim:

1. Method of measuring and/or monitoring the surface tension of a fluid, in which standing capillary waves are produced on the surface of the fluid by means of an oscillation generator of a known frequency and are optically evaluated, characterised by the following features:
    (a) a circular region of the surface of the fluid is excited centrally or peripherally by the oscillation generator;
    (b) the wavelength of the capillary waves thus produced or the radius of the excited circular surface region is altered until a system of circular standing capillary waves is produced; and
    (c) the occurrence of circular standing capillary waves is determined by measuring the intensity of light radiation reflected on the surface of the fluid.

2. Method as claimed in claim 1, characterised in that the wavelength of the generated capillary waves is altered by altering the frequency of the oscillation generator while keeping the diameter of the excited circular surface region constant.

3. Method as claimed in claim 1, characterised in that the radius of the excited circular surface region is altered while the frequency of the oscillation generator is kept constant.

4. Method as claimed in claim 3, characterised in that the alteration of the radius of the excited circular surface region is achieved by alteration of the filling level of a conical vessel.

5. Method as claimed in claim 1, characterised in that the light radiation covers the range of several wave trains simultaneously.

6. Method as claimed in claim 1 or 2, characterised in that for calibration of a measuring and/or monitoring device operating according to this method the relationship between the frequency at which the standing capillary waves occur and the respective surface tension is determined in such a way that for several fluid samples of differing surface tension the frequency and the wavelength at which standing capillary waves occur is determined in each case and from this the surface tension is calculated.

7. Method as claimed in claim 1, characterized in that said fluid includes water.

8. Method as claimed in claim 1, characterized in that said fluid includes alcohol.

* * * * *

UNITED STATES PATENT AND TRADEMARK OFFICE
CERTIFICATE OF CORRECTION

PATENT NO. : 4,512,183
DATED : April 23, 1985
INVENTOR(S) : Martin Alexander

It is certified that error appears in the above-identified patent and that said Letters Patent are hereby corrected as shown below:

Column 1, line 38, change "X = density" to -- P = density --.

Signed and Sealed this

Twenty-seventh Day of August 1985

[SEAL]

Attest:

DONALD J. QUIGG

Attesting Officer     Acting Commissioner of Patents and Trademarks